United States Patent
Blankenstein et al.

(10) Patent No.: US 9,216,413 B2
(45) Date of Patent: Dec. 22, 2015

(54) PLASMA SEPARATION RESERVOIR

(75) Inventors: Gert Blankenstein, Dortmund (DE); Christian Schoen, Dresden (DE)

(73) Assignee: BOEHRINGER INGELHEIM MICROPARTS GMBH, Dortmund (DE)

( * ) Notice: Subject to any disclaimer, the term of this patent is extended or adjusted under 35 U.S.C. 154(b) by 187 days.

(21) Appl. No.: 13/381,148

(22) PCT Filed: Jun. 8, 2010

(86) PCT No.: PCT/EP2010/058019
§ 371 (c)(1),
(2), (4) Date: Feb. 7, 2012

(87) PCT Pub. No.: WO2011/003689
PCT Pub. Date: Jan. 13, 2011

(65) Prior Publication Data
US 2012/0118392 A1    May 17, 2012

(30) Foreign Application Priority Data
Jul. 7, 2009  (EP) ..................................... 09008837

(51) Int. Cl.
*B01D 63/00* (2006.01)
*B01D 17/00* (2006.01)
(Continued)

(52) U.S. Cl.
CPC ..... *B01L 3/502738* (2013.01); *B01L 3/502746* (2013.01); *B01L 3/502753* (2013.01);
(Continued)

(58) Field of Classification Search
CPC ............ G01N 33/491; B01L 3/502738; B01L 3/502746; B01L 3/50273; B01L 2300/0816; B01L 2300/0681; B01L 2300/165; B01L 2300/087; B01L 2300/0864; B01L 2400/0406
USPC ................. 422/68.1, 502–507, 527
See application file for complete search history.

(56) References Cited

U.S. PATENT DOCUMENTS 6,632,399 B1 * 10/2003 Kellogg et al. ................. 422/72
6,637,463 B1    10/2003 Lei et al.
(Continued)

FOREIGN PATENT DOCUMENTS

CA    2323424 A1    9/1999
EP    0974840 A2    1/2000
(Continued)

OTHER PUBLICATIONS

International Search Report for corresponding PCT/EP2010/058019; date of mailing: Jan. 19, 2011.
(Continued)

*Primary Examiner* — Lyle Alexander
*Assistant Examiner* — Jennifer Wecker
(74) *Attorney, Agent, or Firm* — Michael P. Morris; Mary-Ellen M. Devlin (57) ABSTRACT

The invention relates to a microfluidic apparatus for producing a volume flow that is uniform over time in a metering process. In various solution processes or reaction processes it is essential to have a specified given volume flow or mass flow of fluid available to ensure reliable dissolution of the reagent or ensure that the reaction takes place. In microfluidic apparatus in which separation of particles from a fluid, particularly blood, is carried out through a membrane, the volume flow through the membrane decreases continuously. In order to achieve a uniform volume flow during metering, it is envisaged that first of all a reservoir is filled from a first channel, so that the contents of the reservoir can then be fed to the metering process by opening a fluid stop. The emptying of the reservoir takes place with a uniform volume flow of 0.05 microliters per second to 10 microliters per second.

16 Claims, 8 Drawing Sheets

(51) Int. Cl.
*B01D 29/00* (2006.01)
*B01D 35/00* (2006.01)
*G01N 33/50* (2006.01)
*G01N 33/49* (2006.01)
*B01L 3/00* (2006.01)
*E03B 7/07* (2006.01)
*G01N 33/543* (2006.01)
*G01N 33/558* (2006.01)

(52) U.S. Cl.
CPC ........... *G01N33/491* (2013.01); *B01L 3/50273* (2013.01); *B01L 2200/0605* (2013.01); *B01L 2200/0621* (2013.01); *B01L 2200/0684* (2013.01); *B01L 2300/0681* (2013.01); *B01L 2300/087* (2013.01); *B01L 2300/0816* (2013.01); *B01L 2300/0864* (2013.01); *B01L 2300/165* (2013.01); *B01L 2400/0406* (2013.01); *B01L 2400/0487* (2013.01); *B01L 2400/0688* (2013.01); *B01L 2400/086* (2013.01); *B01L 2400/088* (2013.01); *Y10T 137/0318* (2015.04); *Y10T 137/794* (2015.04)

(56) References Cited

U.S. PATENT DOCUMENTS

| | | | |
|---|---|---|---|
| 7,094,354 B2 * | 8/2006 | Pugia et al. | 210/787 |
| 7,134,453 B2 * | 11/2006 | Peters et al. | 137/806 |
| 7,238,534 B1 * | 7/2007 | Zimmer | 436/169 |
| 2002/0114738 A1 | 8/2002 | Wyzgol et al. | |
| 2004/0037739 A1 * | 2/2004 | McNeely et al. | 422/58 |
| 2004/0206408 A1 | 10/2004 | Peters et al. | |
| 2004/0209381 A1 * | 10/2004 | Peters et al. | 436/177 |
| 2005/0249641 A1 * | 11/2005 | Blankenstein et al. | 422/102 |
| 2007/0269893 A1 * | 11/2007 | Blankenstein et al. | 436/2 |
| 2008/0257754 A1 * | 10/2008 | Pugia et al. | 205/792 |
| 2009/0227041 A1 * | 9/2009 | Wang et al. | 436/180 |
| 2010/0089529 A1 * | 4/2010 | Barholm-Hansen et al. | 156/247 |
| 2011/0045505 A1 * | 2/2011 | Warthoe et al. | 435/7.92 |

FOREIGN PATENT DOCUMENTS

| | | | | |
|---|---|---|---|---|
| EP | 974840 A2 * | 1/2000 | | G01N 33/52 |
| EP | 1062042 | 12/2000 | | |
| JP | 2002243748 A | 8/2002 | | |
| JP | 2006511809 A | 4/2006 | | |
| JP | 2008076306 A | 4/2008 | | |
| JP | 2009014439 A | 1/2009 | | |
| WO | 9324231 A1 | 12/1993 | | |
| WO | 9946045 A1 | 9/1999 | | |
| WO | 2008127191 A1 | 10/2008 | | |

OTHER PUBLICATIONS

Abstract in English of JP2009014439, Jan. 22, 2009.

\* cited by examiner

PLASMA SEPARATION RESERVOIR

The invention relates to a microfluidic apparatus for producing a volume flow that is uniform over time in a metering process. The invention can be used in microfluidic apparatus employed for plasma separation.

In the separation of particles from a fluid, such as the separation of blood, for example, the medium which is to be separated, in this case blood, is fed into a filter. The fluid and any small ingredients flow through the filter and are carried away through channels in the apparatus. In order to detect specific properties of the fluid, the fluid is brought into contact with reagents that give rise to a chemically or physically detectable interaction, e.g. staining of the fluid in the case of a detection reaction.

For these various wet-chemical, biochemical or diagnostic analyses it is necessary for the fluid to be mixed with reagents for a specified length of time in a chamber or reservoir and thereby to dissolve these reagents and/or react with them.

Moreover, in various solution or reaction processes of this kind it is essential to have a specified given volume flow or mass flow of fluid available to ensure reliable dissolution of the reagent or to ensure that the reaction takes place.

If the fluid current is less than that which is necessary, for example, there is a danger that components of a dried, more particularly powdered substance contained in the microfluidic analysis apparatus will clump together or stick as deposits. This may cause the results of a detection reaction to be falsified.

Against this background, an object of at least preferred embodiments of the invention is to provide a given amount of fluid which is to be investigated for a given time span in an investigation area.

The preferred embodiments of the invention also set out to provide microfluidic apparatus such that a given volume flow of a fluid takes place uniformly over a predetermined length of time.

The invention relates to a microfluidic apparatus having the features of claim 1.

The microfluidic apparatus according to the invention makes it possible to provide a volume flow of fluid that is uniform over time. For this purpose, the apparatus comprises means for separation, particularly for filtering blood and comprises a first channel which receives the separated fluid and carries it away.

In an end region, the first channel is adjacent to stop means, particularly a fluid stop or capillary stop, which can halt the flow of fluid in the first channel for a given length of time. Upstream, adjacent to the first channel and adjacent to the fluid stop, a second channel branches off from the first channel. The second channel forms a connection to a reservoir.

The stop means or fluid stop in the microfluidic arrangement according to the invention is preferably a capillary stop, as known for example from EP 144 1131 A3.

The fluid stop preferably has the particular design feature that the geometry of a fluid-carrying element abruptly changes at the fluid stop, e.g. by the formation of a step. A fluid stop may also be formed by a sudden change in the wetting characteristics of a fluid-carrying element, e.g. as a result of certain areas being coated with a hydrophilic or hydrophobic material.

The separating means is preferably a membrane or a filter.

In order to operate the microfluidic apparatus in an analyser, for example, a quantity of fluid is fed into an inlet opening of the apparatus. This may be, for example, a drop of blood with a volume of 20 microliters.

Arranged in the inlet opening may be a membrane or a filter into which the supplied medium flows.

The fluid current is transported, in particular, in the vertical direction of flow through pores and capillaries in the filter or membrane.

This reference to a vertical direction means that the flow is substantially perpendicular to the substrate plane of an in particular plate-shaped microfluidic metering device.

Thus the flow passes through a membrane essentially in the direction of thickness.

The membrane or the filter is preferably arranged in the vertical direction between the inlet opening and an inlet chamber located under the membrane/filter.

The membrane or the filter can absorb liquid by the capillary action of its pores or capillaries and retain larger particles which are larger in size than the pores or capillaries.

The pores become partially closed off by the agglomeration of the retained particles, so that the cross-section of flow available for the throughflow decreases constantly as the separation process progresses.

This causes a reduction in the flow rate of the volume flow of fluid in the microfluidic apparatus.

If, for example, the flow volume is initially 0.3 microliters per second when a quantity of 40 microliters of blood is added, this value decreases continuously, so that after 20 seconds only 0.1 microliters per second can pass through the filter or membrane and enter a channel adjacent to the inlet chamber.

Advantageously, the inlet chamber may contain reagents which are dissolved by the fluid current.

Similarly, the membrane may also be soaked in or impregnated with reagents, e.g. reagents that prevent the blood from clotting. When the fluid is added, separation takes place in the membrane thus treated, while at the same time a first reagent is dissolved, the first reagent affecting the biological and/or chemical and/or physical properties, particularly the viscosity of the fluid.

In the inlet chamber there may be a second reagent which brings about a detection reaction in the fluid. This may be an optical colour change, for example.

As the membrane or the filter has a high inherent capillarity, means may be provided for helping the volume flow to run vertically down into the adjacent inlet chamber. For this purpose the inlet chamber may advantageously comprise one or more pillars or posts which have one or more notches extending in the vertical direction.

The pillars or posts are arranged such that the membrane rests on the pillars or posts. The height of the pillars or posts may advantageously correspond to the depth of the inlet chamber, the depth of which is preferably 10 microns to 1000 microns, in particular 50 microns to 500 microns.

The notches on the pillars or posts are in fluidic contact with the membrane that is to be contacted and by their capillary action conduct fluid out of the membrane to the base of the chamber, so that the chamber is wetted. Alternatively or additionally, the membrane may be convex in shape, the height of the convexity corresponding to the depth of the chamber, so that the membrane abuts on the apex of the convexity on the base of the chamber.

As the apex of the membrane forms an acute angle with the chamber base, high capillary forces are produced there during the wetting of the membrane, so that separated fluid is carried away into the chamber through the gap between the membrane and the base of the chamber.

Advantageously, the chamber may be at least partly surrounded by a trench which is deeper than the depth of the chamber and has an air vent so that the air in the inlet chamber can be displaced by the incoming fluid over the trench. The trench is preferably from 100 to 1000 microns wide and 200 to 1000 microns deep.

The volume of the inlet chamber is preferably 0.1; 0.2; 0.5; 1; 2; 5; 10; 20; 50; 100; 200; 500; or 1000 microliters, while it is also possible to select chamber volumes that are obtained by adding the specified values together.

In order to carry the fluid out of the inlet chamber into one or more fluid channels, the channel may widen out in a funnel shape towards the inlet chamber in the connecting region. First of all the width of the channel opens out in the narrow part of the funnel and then increases conically towards the chamber.

Advantageously, in the widened conical part of the funnel, structural elements may be provided, such as the above-mentioned posts or pillars, which can assist with the transport of fluid into the funnel.

The fluid transport is assisted for example by the fact that a gap is formed between a structural element and a funnel wall, so that a capillary force acts on the fluid through the gap. Advantageously, the distance between a pillar wall or a post wall and the funnel wall, i.e. the gap width, may be from 5 microns to 500 microns.

The trench described hereinbefore forms a fluid stop, as the fluid current cannot flow over the trench step. Advantageously, the trench may surround the inlet chamber completely, apart from the funnel-shaped outlet region of the inlet chamber, so that the air can be uniformly displaced from the inlet chamber.

In the region between the chamber outlet funnel and the ends of the trench, which are adjacent to one another, there is a danger that there will be an undesirable outflow of fluid into the trench. Advantageously, therefore, it is envisaged that the ends of the trench should be widened out to prevent an in particular vertical flow from the funnel walls to the trench.

The fluid transported by the first channel adjoining the inlet chamber flows as far as the fluid stop described hereinbefore.

Branching off the first channel is a second channel which connects a reservoir to the first channel.

On reaching the fluid stop, the fluid flowing out of the inlet chamber flows into the reservoir and may fill it to a given level, advantageously to a level of 50% to 100%. When the level is reached, the fluid stop may be closed off and the fluid from the reservoir may flow continuously through the second channel and the fluid stop into an outlet channel.

The outlet channel may be connected to the fluid stop downstream.

Thanks to the intermediate reservoir a volume flow of the fluid can be achieved which is uniform over time.

As the volume flow is greatly reduced as time passes during the separation of the starting medium, the reservoir serves to compensate for this reduction in the volume flow.

The reservoir or intermediate store fills up with the separated fluid. Advantageously, a specific quantity of fluid is taken up by the reservoir, which may have a capacity of 0.1 microliters, 0.2 microliters, 0.5 microliters, 1 microliters, 2 microliters, 5 microliters, 10 microliters, 20 microliters, 50 microliters, 100 microliters, 200 microliters, 500 microliters, 1000 microliters or a fraction or multiple thereof.

Advantageously, in the case of quantities of fluid such as a drop of blood, a reservoir volume of from 0.5 microliters to 10 microliters may be provided.

In order to hold a larger amount of fluid than the channels can, the reservoir may be deeper than the first channel, which is also referred to as the supply channel or feed channel. In particular, the depth of the reservoir may be 1.2 to 5 times the depth of the first channel.

The second channel, which forms the supply from the first channel to the reservoir, may widen out in the inlet region of the reservoir. The depth of the second channel may correspond to the depth of the first channel at the branching point. Advantageously, steps or terraces may be provided in the conically widening connecting region to the reservoir. Alternatively, the depth in the inlet or connecting region of the reservoir may increase in the manner of a ramp, so that the fluid flowing into the second channel flows along the ramp or step to the bottom of the reservoir and fills the deeper reservoir interior.

To ensure a uniform flow of the fluid into the reservoir and prevent the formation or inclusion of air bubbles, the reservoir may be laterally bounded by a trench.

The geometric shape of the reservoir may be advantageously such that the front of the fluid current encloses an angle of less than 90 degrees to the trench, so that the fluid front runs along the edge of the trench during filling.

Alternatively, however, inflow angles of 90 degrees would also be acceptable.

In the outlet from the reservoir, i.e. the area of the reservoir that is filled last in the event of total filling, a third channel, a so-called trigger channel, may advantageously branch off. The trigger channel is connected both to the reservoir outlet and to the fluid stop. The trigger channel may have a smaller cross section of high capillarity compared with the reservoir. The trigger channel provides a fluidic connection between the fluid stop and the reservoir outlet, while a fluid transport from the reservoir flows via the channel into the fluid stop.

Advantageously, the fluid stop may have a half-funnel or tub shape with a rising base. The depth of the half-funnel or tub may be 100 to 500 microns at the deepest point.

At the top of the deep part, the first channel may open into the wall above the bottom of the fluid stop. The trigger channel may open into a flat, rising section of the fluid stop and have a depth of from 5 microns to 100 microns, in particular from 30 microns to 70 microns.

The flat region of the fluid stop may be advantageously delta-shaped, the delta being a ramp in the depthwise direction. The ramp connects the deep regions of the fluid stop to the mouth of the trigger channel.

The fluid stop can be filled by means of the trigger channel.

As soon as the fluid level in the chamber of the fluid stop reaches the height of the first channel, the fluid stop is bridged and the fluid stored in the reservoir flows away through the second channel and the outlet channel.

Advantageously it is also possible for the reservoir to be used as the reaction chamber. For this, reagents may be deposited in the reservoir chamber, e.g. by incorporation and/or drying. While the reservoir is being filled and during the subsequent dwell time, chemical or biological reactions can then take place in the reservoir, assisted, for example, by the use of catalysts, or the supply of light and/or heat.

The dwell time of the fluid in the reservoir may be determined by the fill speed and the flow rate of the fluid current in the trigger channel.

The dwell time or reaction time in the reservoir is between 5 seconds and 2000 seconds.

As the fluid that has flowed into the trigger channel remains there, on account of the high capillarity of the channel, the volume of the trigger channel should not exceed 5% of the volume of the reservoir.

The reservoir may also have the function of generating a constant volume flow over time for dissolving a reagent. The reagent is deposited in a channel or a storage chamber downstream of the fluid stop.

With reagents, particularly in powder form, it is often necessary to build up a volume flow which ensures reliable dissolution in the fluid by the flow of the substance, particularly the powder.

Particularly with these powdered substances, sticking may occur, which may require a reagent to initiate the dissolving process and break up a clump. This dissolving process can only be achieved by means of a sufficiently large volume of fluid being transported: a flow rate of 0.1 microliters to 10 microliters per second is envisaged depending on the substance, the quantity of fluid and the quantity of material.

Alternatively and/or in addition to the geometric configuration of the capillary stop, the latter may also be formed by a hydrophobic section of channel. For this, a part of the first channel may be provided with a hydrophobic coating or, if there is a provision to hydrophilise the channel system, one section of channel may be excluded from this hydrophilisation.

The fluid interface of an aqueous liquid flowing through the first channel is prevented from progressing in the hydrophobic region as the wettability of the channel is sharply reduced at that point.

Advantageously, the hydrophobic region may have a rough surface to which small fluid particles can adhere physically. The adhesion of the particles improves the wettability of the region, so that the region which was originally hydrophobic is wetted within a specified time span and the fluid is able to flow over the stopping point.

This wetting can also be caused or assisted by chemical reactions, for example by additionally coating the hydrophobic section of channel with a ligand to which fluid constituents bind, with the result that the wetting increases continuously.

Within the time period during which the continuous wetting takes place, advantageously a reservoir of the type described hereinbefore may be filled.

After the capillary stop has been overcome, the quantity of fluid stored intermediately in the reservoir is available for further analytical, diagnostic or testing procedures. Advantageously, the reservoir may be geometrically designed such that reliable filling and emptying are guaranteed.

For this purpose it is advantageous for the reservoir chamber to be substantially spherical, funnel-shaped or triangular in form, widening out in cross section from the inlet region. Then, when the reservoir is filled, the fluid interface widens out continuously. The reservoir preferably has an asymmetrical shape at its end, in relation to the propagation front of the fluid. By the end of the reservoir is meant the region of the reservoir which is filled last, when the reservoir is filled completely. This is, in particular, a region adjoining a lateral ventilation trench. This ensures that the direction of propagation of the interface, i.e. the direction of flow of the fluid front, turns during the filling of the reservoir in the direction of the end region, particularly advantageously in the direction of an outlet channel or trigger channel.

The reservoir meanwhile is filled completely, while the air present in the reservoir is displaced via the lateral trench.

During emptying, the process is reversed.

The reduction in the width of the meniscus in the inflow and outflow region of the reservoir assists with the emptying, as the shortening of the interface exerts an assisting compressive force by the release of energy during the shortening.

Preferred embodiments of the invention will now be described more specifically by way of example only and with reference to the attached drawings.

They show:

FIGS. 14*a* and 14*b*: An inlet region into a feed channel A microfluidic apparatus (1) comprises an inlet chamber (2) which is provided with a device (3) for separating particles. A microporous membrane (3) for example is used as the separating device or filter.

The membrane material is selected from among from materials such as glass fibre membranes, cellulose based membranes, nitrocellulose membranes, nylon membranes or synthetic polymer material, while mixtures of materials may also be used.

Figure 8:
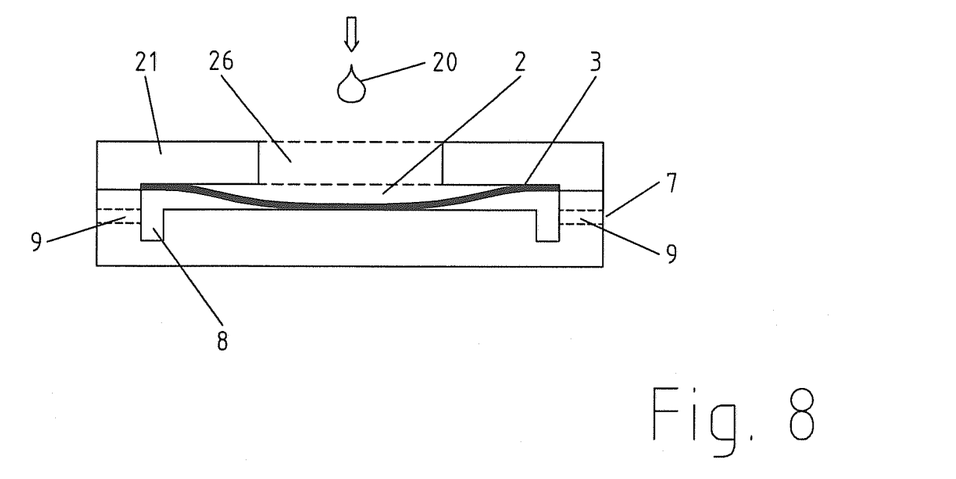
FIG. 8. An inlet region in cross-section

FIG. 8 shows an inlet chamber (2), which is covered by a lid (21) with an inlet opening. The lid (21) is fixed on a substrate carrier (7). A connection between the lid (21) and the carrier (7) is obtained by adhesion or bonding or welding, while advantageously a double-sided adhesive film may also be used as the connecting layer.

Organic plastics, in particular, such as polydimethylsiloxane (PDMS), polymethylmethacrylate (PMMA), polystyrene, polycarbonate and inorganic substances such as glass, quartz and ceramics may also be used as the materials for the lid and substrate carrier.

The membrane (3) is preferably secured in a recess on the lid (21).

The membrane (3) is used functionally for filtering a liquid that contains particles, particularly blood.

During this separation process a laminar flow of the fluid flows vertically through the membrane (3). The membrane (3) may be provided with reagents, for example a coating which has been dried onto the membrane fabric. During the filtration, a specific amount of fluid (20) is fed into the inlet opening (26).

The fluid (20) is taken up by the membrane (3) and a separated quantity of fluid flows through the membrane (3), which, as shown schematically in FIG. 8, is particularly advantageously in contact with the base of the inlet chamber (2).

Advantageously, during the throughflow process, reagents from the membrane (3) dissolve in the fluid and/or are carried along with the current of fluid, even if they are not dissolved therein.

As a result, chemical and/or biological reaction processes and/or physical transport processes are initiated, such as an ion exchange or binding or adsorption of fluid components to the membrane (3).

The contact of the membrane (3) with the base of the inlet chamber (2) results from the bending or convexity of the membrane (3) in the direction of the base. As a result, small angles are formed between the base and the membrane in the contact region, producing high capillary forces at this point, so that fluid is sucked out of the membrane (3) into the contact gap and, as a result of this wetting, fills the chamber (2).

Figure 7:
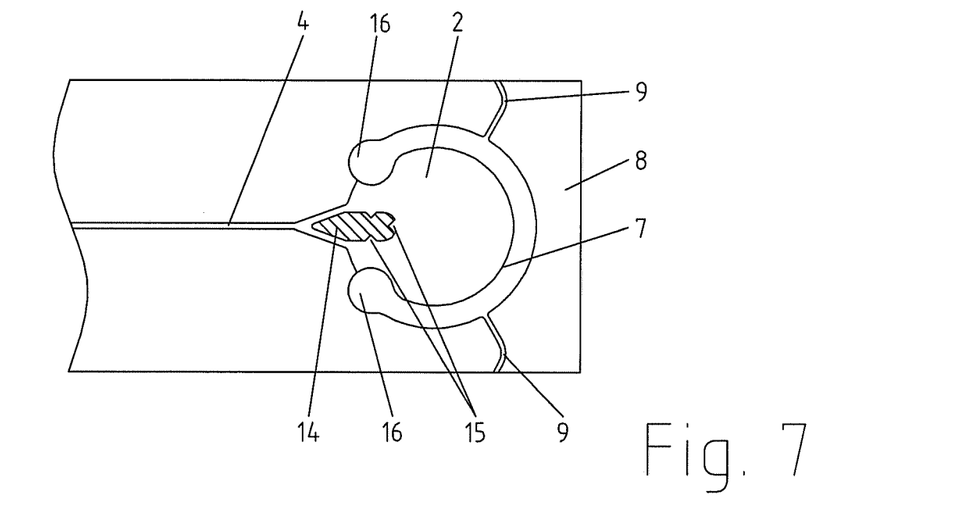
FIG. 7: An inlet region of a microfluidic apparatus with adjacent trench

In order to start a vertical flow of fluid through a membrane (3), it may also be envisaged, by way of assistance, to provide structural elements (14) with vertical notches (15) in the inlet chamber (2), as shown in FIG. 7. The structural element (14) is a post, the tip of which extends into the mouth region of the first channel (4) and which has a number of vertical notches (15) on its outer surface.

The inlet chamber (2) is preferably circular. The chamber (2) is bounded at its sides by a trench (8) which extends to a depth of 200 microns to 1000 microns, in particular 300-600 microns, from the level of the base of the chamber. Branching off from the trench (8) are two ventilation channels (9), these ventilation channels being connected to the outer edge of the microfluidic apparatus (1). Alternatively, the trench (8) may have one vent or more than two vents.

The membrane (3) is located at least partly on the structural element (14), as a result of which the fluid taken up by the membrane (3) comes into contact geometrically with the vertical notches (15). As a notch (15) has a high capillary force by virtue of its acute angle of opening, fluid is sucked out of the membrane (3) into the capillary gap of a notch (15) and flows vertically along the notch (15) towards the base of the inlet chamber (2), which it then wets.

The transition region (18) between the inlet chamber (2) and the first channel (4), which transfers the fluid from the chamber (2) into the fluidic channel system of the apparatus (1), is of triangular, delta-shaped or funnel-shaped configuration.

The fluid, which has been transferred either directly and/or by means of structural elements (14) from the membrane (3) into the chamber (2), flows via the transition region (18) into the feed channel (4).

A homogeneous bubble-free inflow of fluid is assisted by the structural element (14), as a result of the top of the element (14) projecting into the triangular inlet section of the feed channel (4) so as to form two inlet channel sections to the feed channel (4).

As the trench (8) is interrupted in the mouth or transition region (18) to the feed channel (4), there is an increased risk, in the end regions of the trench (8), that there will be an accidental discharge of fluid into the ventilation trench (8).

To counteract this, the end (16) of the trench is made wider.

As shown in FIG. 7, the end (16) of the trench is widened in a circular configuration, although other shapes such as an elliptical form would also be possible. Advantageously, the transitions should be very rounded at their ends, as edges act as vertical notches that could initiate an accidental vertical flow into the trench (8), as mentioned previously.

The average diameter of the widened section should be at least 1.5 to 10 times the width of the trench, so as to increase the barrier effect at this point.

Figure 14A:
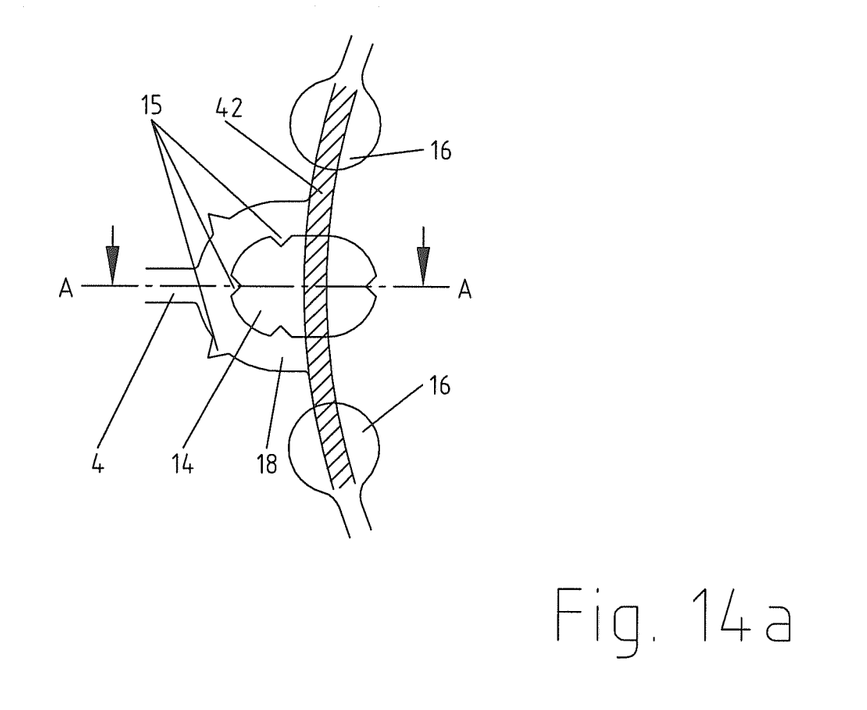
Figure 14B:
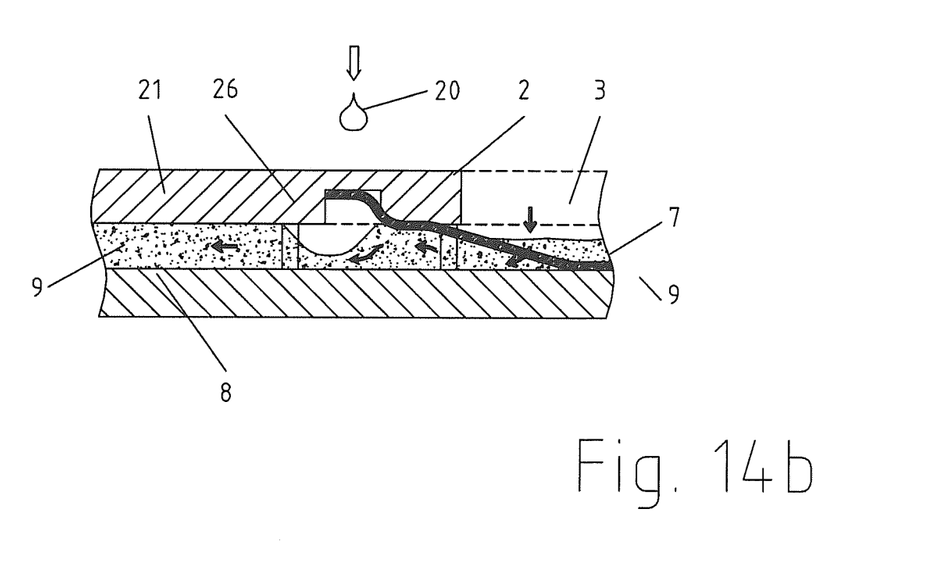

As schematically shown in FIG. 14a, the transition region (18) to the feed channel (4) may also be semicircular or horseshoe-shaped, while the structural element (14) is of matching shape. In the transition region (18) the attachment (42) of the membrane (3) intersects with the entry opening into the first channel (4) substantially at right angles. As schematically shown in FIG. 14b, a quantity of fluid (20), in particular a drop of fluid which has been introduced into the inlet opening (26), is taken up by the membrane (3). Filtered fluid, conjugate of test fluid and reagents deposited in the membrane (3) and/or filtered fluid plasma then flow in the direction of the first channel (4). Particularly advantageously, the membrane (3) rests at least partially on the base under the inlet opening (26), so that acute-angled capillary gaps are formed which assist with the wetting of the base region as a result of the high capillary force in the region of the tip. Advantageously, the apex angle, i.e. the angle of opening between the base plane and the membrane surface is 1, 2, 3, 5, 10, 15, 20, 25, 30, 35, 40, 45 degrees or partial angles of the angular degrees specified.

The attachment (42) of the membrane (3) is effected in a recess (41) in the lid element (21), the membrane being secured in the recess (41) by adhesion, lamination, welding or other means. As shown in FIG. 14b, the area under the membrane (3) is initially wetted homogeneously. In the region of the recess it may happen that the homogeneous three-dimensional wetting comes to a halt owing to the enlargement of the cross-section and/or because of altered wetting properties of the attachment (42). In this case, a two-dimensional flow of fluid is produced, with partial wetting of the base and walls of the chambers and/or channels with a decreased flow volume.

In order to achieve the possible flow volume, homogeneous three-dimensional wetting of the structures (4, 5, 6, 12) that carry the fluid is advantageously re-established. For this purpose, downstream of the inlet opening (26) are provided one or more vertical fluid-conveying structural elements (15), particularly notches. The vertical fluid-carrying structural elements cause vertical flow between the bottom and top, as schematically shown in FIG. 14b, thus achieving three-dimensional wetting.

The structural elements (15) may be notches and/or pillars which extend uniformly between the base and top and are arranged relative to one another such that vertical capillary gaps of high capillarity are formed. Particularly preferably, vertical notches (15) are arranged on the outer surface of the structural element downstream of the attachment.

Alternatively or additionally, it is also possible to provide notches (15) or vertical conveying elements (15) of this kind in the wall surface of the transition region (18). It is also advantageously possible to produce the structural element and/or the substrate carrier from a hydrophilic material and/or to provide the surfaces of the fluid-conveying structures with a hydrophilic coating.

From the transition region, the fluid or fluid mixture enters the first channel (4), hereinafter also called the feed channel (4).

Figure 1:
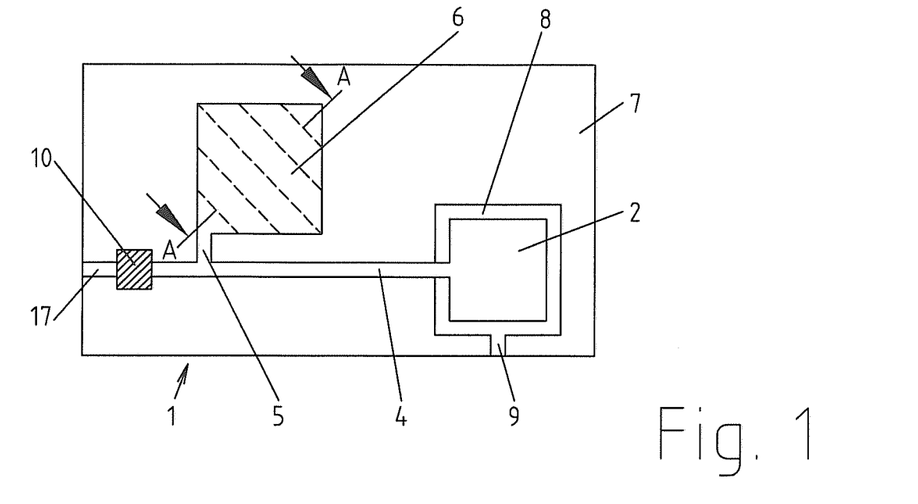
FIG. 1: A microfluidic apparatus with a reservoir and a fluid stop

The fluid transported away through the feed channel (4) flows as far as a fluid stop (10), as can be seen from FIG. 1. The fluid stop (10) is preferably embodied as a time-limited stopping area for the fluid so that the latter can fill a reservoir (6).

During the filtering process using a membrane (3), the volume flow through the membrane (3) decreases in the course of the filtering, as the pores and channels of the membrane become clogged. A time function of the filter flow in the feed channel (4) with a continuously decreasing flow rate can be inferred from FIG. 6, curve A. If the fluid volume flow after the addition of 20 μl fluid onto a membrane is still 0.1 to 0.2 microliters per second to begin with, this value decreases to 0.05 to 0.02 microliters per second after about 30 seconds.

In dissolution processes, however, a specific volume flow is usually necessary in order to ensure reliable dissolution of a substance that is required for a detection reaction, for example.

Figure 10:
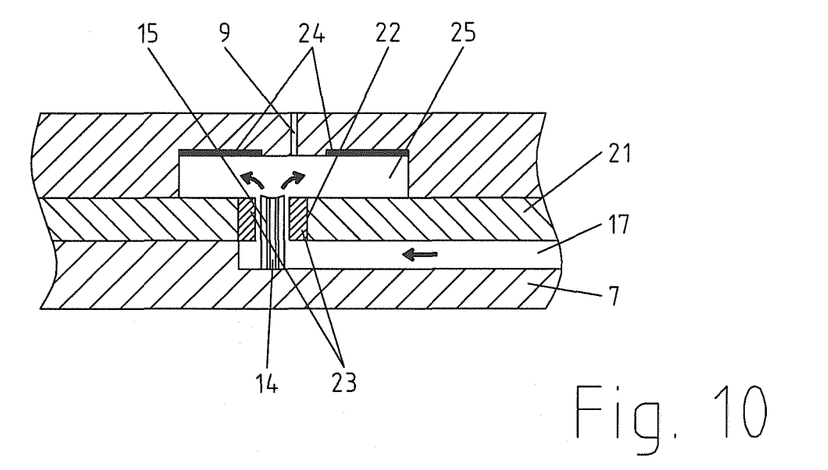
FIG. 10: An analysis chamber with vertical inflow

FIG. 10 shows an analysis region of a microfluidic apparatus (1) in cross-section. In an outlet channel (17), which is fluidically connected to the feed channel (4), a structural element (14) with notches (15) is arranged at the end thereof.

The structural element (14), in this case a pillar, projects into a vertical throughflow opening (22) in a lid (21). The throughflow opening (22) is annularly filled with a reagent substance (23) in the outer region. Alternatively, the throughflow opening may also be filled with the reagent substance up to a predetermined fill level.

Alternatively, the reagent may also be deposited in an annular configuration on the walls and/or in a disc-shaped configuration on the ceiling of the analysis chamber (25) and/or deposited in the second channel.

Figure 9:
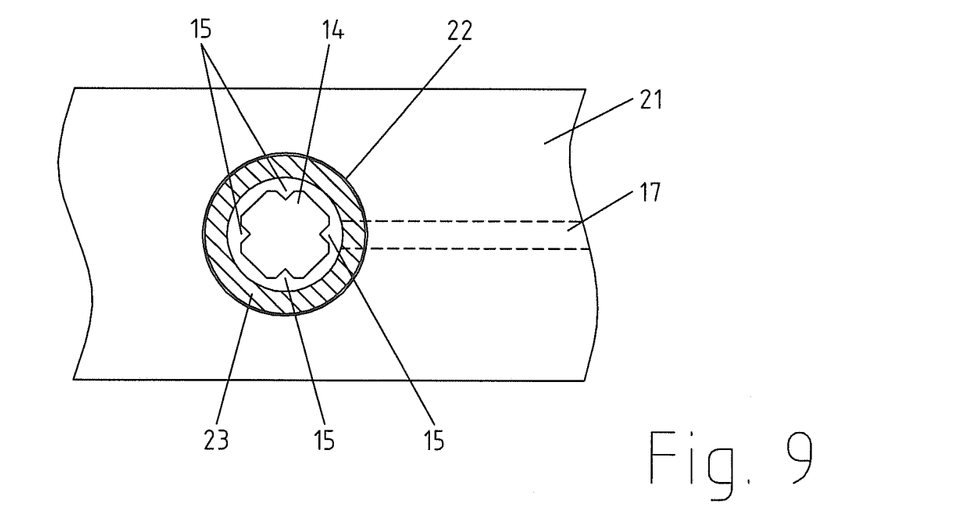
FIG. 9: A reagent store with fluid carrying structures

FIG. 9 is a plan view of the throughflow opening (22) with the reagent (23) contained therein and a pillar (14) immersed in the reagent (23).

Notches (15) in the pillar (14) bring about a vertical flow which also allows flow to take place counter to gravity. The pillar walls enclose a capillary gap with the substance of the reagent (23), which also assists the vertical flow. The reagent preferably has a porous consistency, so that the fluid flowing vertically upwards moistens the substance, penetrates it and dissolves it in the volume flow of the fluid.

The dissolved fluid flows into an analysis chamber (25) as shown in FIG. 10. The mixture of fluid and reagent fills the chamber (25). Properties of the fluid/reagent mixture can then be determined using detectors (24).

A minimum volume flow of fluid required to dissolve the reagent is 0.01; 0.02; 0.03; 0.04; 0.05; 0.1; 0.2; 1; 2; 5; 10; 20; 50; 100 microliters per second or a multiple or fraction thereof. In analytical systems that detect the properties of blood plasma with dropwise addition, fluid volume flows of 0.01 to 0.5 microliters per second are used.

Advantageously, in embodiment 1 according to FIG. 1, it is envisaged that a reservoir (6) should first be filled with the separated fluid, in order for the reservoir (6) to then be emptied at a constant volume flow.

In order to fill a reservoir (6) with a predetermined amount of fluid, a fluid stop (10) is arranged along the transporting path of the first channel (4) or feed channel (4).

The fluid stop (10) prevents the fluid from flowing onwards for a specified length of time or a filling time within which the reservoir (6) is totally filled. The reservoir (6) is filled by means of a second channel (5) which widens out towards the chamber of the reservoir.

Figure 11:
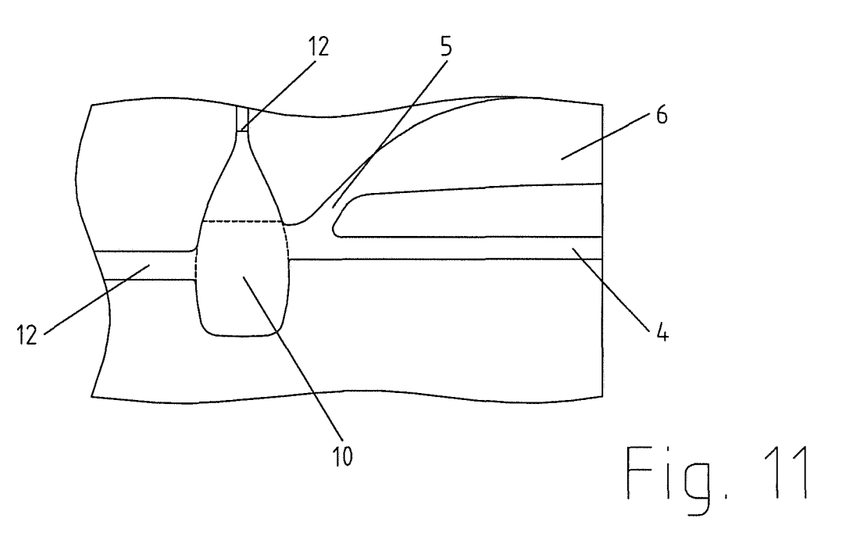
FIG. 11: Connecting regions to a capillary stop

The second channel (5) branches off from the first channel (4), this branching taking place upstream of the fluid stop (10). Alternatively, the second channel (5) may end in a region that connects the first channel (4) to the fluid stop (FIG. 11) or in another embodiment (not shown) it may also be branched, one branch being connected to the first channel (4) and a second branch to the fluid stop (10).

A feature common to these arrangements of the second channel (5) or inflow channel to the reservoir (6) in relation to the fluid stop (10) is that a short flow path is produced between the reservoir (6) and the fluid stop (10).

The reservoir (6) may also be used as a reaction chamber. For this purpose, reagents such as powders or a dried-in test substance may be placed in the reservoir (6).

Figure 2:
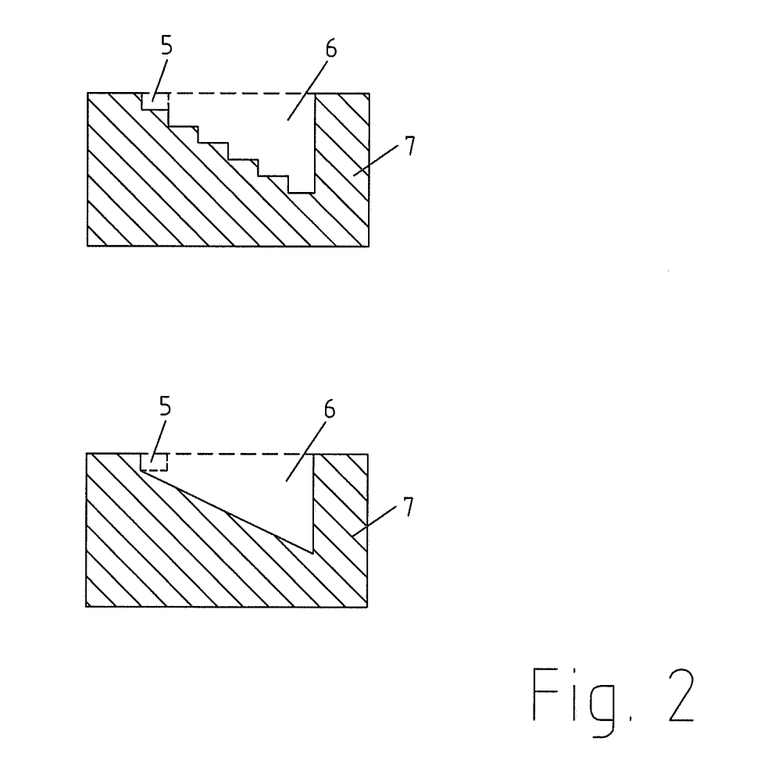
FIG. 2: An embodiment of a reservoir according to the invention in cross-section

The volume of the reservoir chamber (6) is such that the chamber can absorb more than 50% of the quantity of fluid added. To provide the largest possible reservoir volume, it is advantageously envisaged that the depth of the chamber (6) increases, starting from the reservoir channel (5) or second channel (5), as shown in FIG. 2, along the section on the line A-A in FIG. 1. Thus the depth of the reservoir (6) may increase by steps, or grow with a ramp-like geometry. The variation in depth may also be limited to a partial region of the reservoir (6), particularly the inlet region into the reservoir (6) at the mouth of the second channel (5).

Advantageously, the reservoir has a volume of 0.1 microliters to 1000 microliters, or 1 microliter to 10 microliters when used for drops of blood.

The volume of the reservoir (6) corresponds to a desired amount of reaction mixture, when it is used as a reaction chamber.

The fluid fills the reservoir chamber (6) as a result of capillary forces or external fluid pressures. An external pressure is applied for example by centrifuging or by means of an external hydrostatic pressure.

The chamber of the reservoir (6) may contain structural elements (14) to generate a uniform distribution of fluid. The depth of the reservoir is preferably 5 microns to 1000 microns, particularly preferably 100 microns to 400 microns.

The fluid stop (10) may be constructed as a so-called time barrier, namely a time gate, while during the stopping time the reservoir is at least partially filled. In reaction processes the reaction takes place during the stopping time. A time gate is produced for example by a hydrophobic section of channel. The stopping of the fluid in the hydrophobic section is based on the fact that the aqueous solution cannot wet the hydrophobic channel section and thus cannot pass over it.

Plastic materials such as polyethylene, polypropylene, polystyrene, polyacrylate, PTFE or silicones form hydrophobic surfaces. Hydrophobic surfaces may also be achieved using coatings, especially nano-coatings. Moreover, nanostructuring of the surface could also be carried out, particularly by irradiation with a UV laser, whereby the surfaces produced by the laser cutting are given a structure with defined wetting properties.

Advantageously the fluid stop (10) contains both hydrophobic and hydrophilic areas on its surface.

In a substrate (7) consisting of one of the above-mentioned materials, in order to produce a hydrophobic section of channel the structures (2; 8; 9; 4; 5; 6) of the chambers and channels are formed in the substrate. The side walls and the base of the feed channel (4) are then hydrophobic.

A hydrophilic material is used for the lid (21), so that the top of the channel is hydrophilic. Alternatively, channels and chambers may also be rendered hydrophobic or hydrophilic by coating, e.g. by spraying.

The time gate is made hydrophilic by the depositing of components from the fluid on the hydrophobic surfaces.

The hydrophilisation of the fluid stop (10) can be coupled with the process of filling the reservoir (6).

For this, hydrophilising reagents (23) are arranged in the reservoir (6), these reagents being dissolved by the incoming fluid and flowing by diffusion into the fluid stop (10). The stopping time of the fluid stop (10) is dependent on the quantity or concentration of the hydrophilising substances.

Once the fluid stop (10) has been removed, the contents of the chamber of the reservoir (6) can flow freely into the outlet channel (17).

Figure 3:
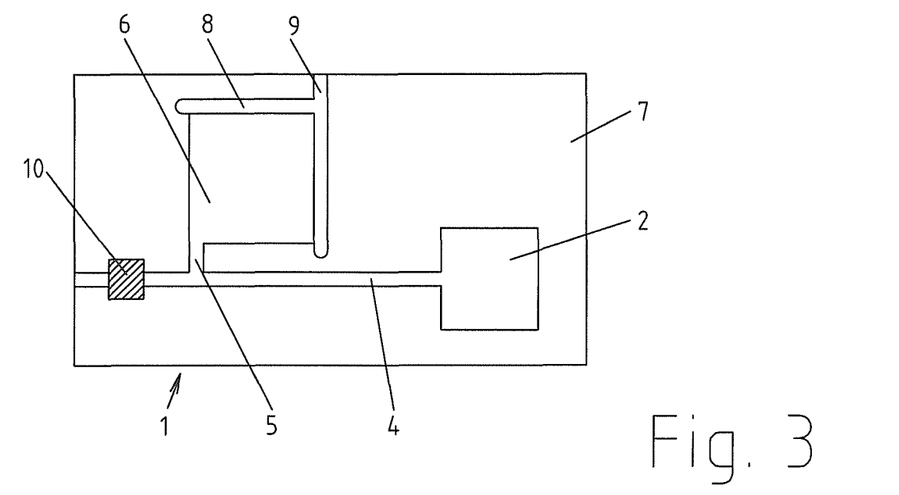
FIG. 3: A reservoir with ventilating trench

Advantageously, the reservoir (6) is bounded on at least one side of the chamber by a trench (8) which is coupled to a ventilation channel (9), as shown in FIG. 3. This enables the reservoir (6) to be filled continuously, as the air is displaced via the trench (8) and the vent (9). In another embodiment according to FIG. 4, a reservoir (6) is provided having a substantially triangular surface, while the side of the surface which is geometrically opposite the inlet or second channel (5) is bounded by a trench (8).

Figure 4:
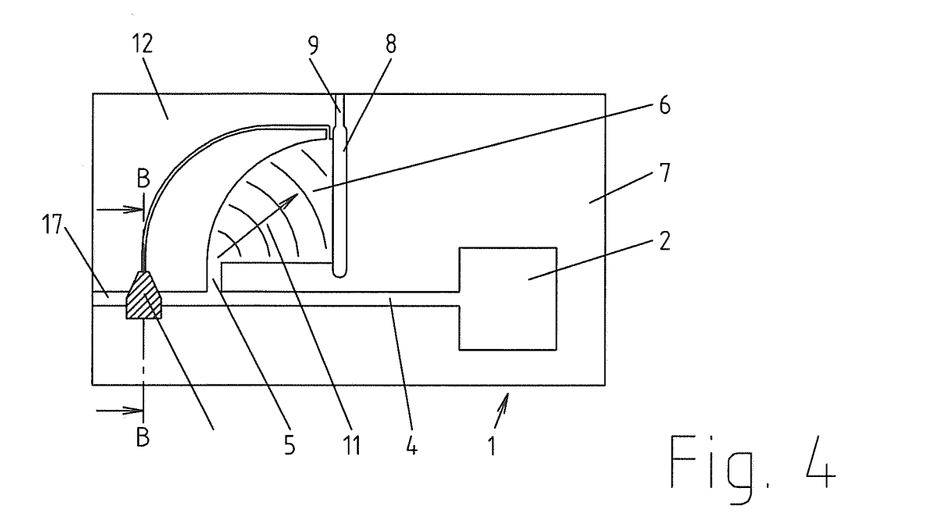
FIG. 4: A reservoir with bypass triggering

The sides of the surface adjoining the channel (5) have walls, the path of the walls having a curvature as shown in FIG. 4.

As the reservoir (6) is filled, the fluid propagates within the chamber (6). The direction of flow (11) of the front, indicated by an arrow, is determined by its chamber geometry, while the surface tension of the fluid minimises the length of the interface.

Figure 12:
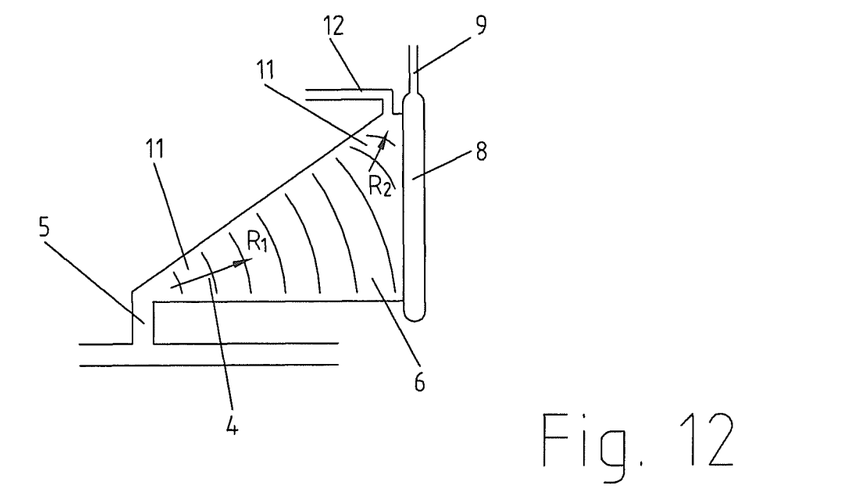
FIG. 12: The propagation of a fluid front in a triangular reservoir

FIG. 12 shows a substantially triangular reservoir (6), which is fed by a second channel (5).

As the reservoir (6) is filled, the interface moves along in the direction of flow (R1, R2) into the reservoir. The fact that the side surfaces of the reservoir (6) adjoining the inflow region are at an angle of less than 90 degrees to one another, while a trench is provided adjacent to a side surface opposite the inflow region, ensures that the reservoir is filled completely.

During the filling, the fluid/gas interface first moves in the direction R1 until the edge of the trench (8) is reached. The gas, particularly air, contained in the reservoir (6) is displaced outwards via the trench (8) and a vent (9). As the fluid front continues to progress, the edge of the trench now forms an additional interface, as described hereinafter.

The partial region of the interface in the reservoir (6), i.e. the fluid front in the reservoir (6), now changes its direction of flow. The side surfaces and trench of the reservoir (6) are arranged relative to one another such that, when the filling of the reservoir is substantially complete, the direction of the flow of fluid faces in the direction of the inlet region of a branch channel (12) or trigger channel (12).

Figure 13:
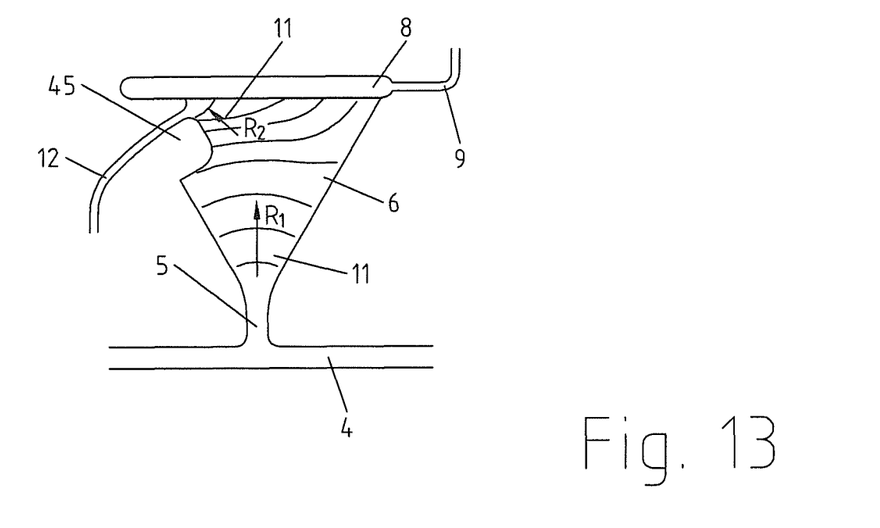
FIG. 13: The propagation of a fluid front in a triangular reservoir with a shaped part on the trigger channel

FIG. 13 shows an alternative embodiment of a reservoir (6) according to the invention. In this embodiment too, total filling of the reservoir (6) is achieved by the fact that the direction of flow (R1, R2) of the fluid front turns during filling. In the embodiment shown in FIG. 13, this is achieved by means of an indentation (45) in the reservoir, which causes the interface to rotate in collaboration with the trench (8). As schematically shown in FIG. 13, the fluid front first migrates substantially vertically into the funnel-shaped reservoir (6), and then the indentation (45) causes the front to turn in the reservoir (6).

Adjacent to the region that is filled last when the reservoir is filled completely, a trigger channel (12) branches off from the reservoir (6), forming an outlet channel (17) for the reservoir (6) and being fluidically connected to the fluid stop (10).

The trench (8) cannot be wetted, on account of being, in particular, 2 to 10 times deeper than the bottom of the reservoir, so that one end of the interface stops at the edge of the trench and then migrates towards the trigger channel (12).

This geometric configuration of the reservoir (6) ensures that the reservoir (6) is filled in bubble-free manner.

The fluid stop (10) according to embodiment example 4 is a capillary stop (10). Connected to the capillary stop (10) are the feed channel (4) or first channel (4), the trigger channel (12) and an outlet channel (17).

Figure 5:
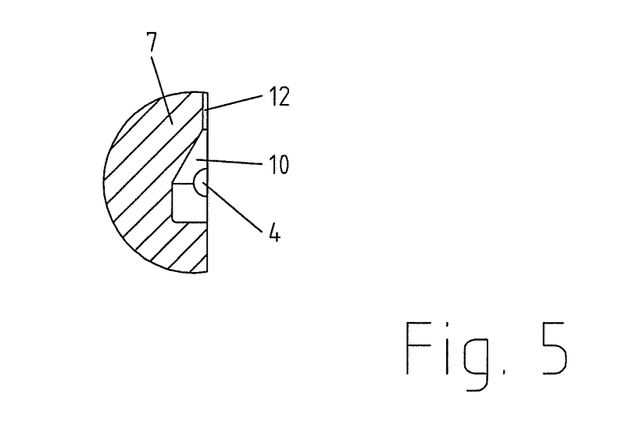
FIG. 5: A cross-section through a capillary stop

The operation of the capillary stop (10) is based on an abrupt increase in the cross-section of the channel. The capillary stop (10) is shown in FIG. 5 in cross section along the section line B-B in FIG. 4.

The capillary stop varies in its depth. In the deepest part of the capillary stop (10), the feed channel (4) opens into the stop (10) on the top of the substrate carrier (7). As can be seen from FIG. 5, the step or edge of the semi-circular channel (4), the channel entrance (13), to the capillary stop (10) acts like the edge of a trench. As the distance of the edge of the channel (4) is large compared with the depth of the capillary stop (10), fluid carried in the feed channel (4) cannot wet the volume of the stop (10). However, the capillary stop (10) can be overcome, as a result of wetting taking place through the trigger channel (12).

The fluid carried through the reservoir (6) by the trigger channel (12) is conveyed into an end region of the fluid stop (10) which corresponds in its depth to the depth of the trigger channel (12). Thus, the aqueous liquid in the trigger channel (12) is able to wet the end region of the fluid stop (10) and flow into the fluid stop (10) along the ramp shown in FIG. 5 and fill this fluid stop. In order to assist the flow of fluid from the trigger channel (12) into the capillary stop (10), structural elements (14) such as pillars or posts may be provided on the ramp surface and the bottom and side surfaces of the capillary stop, at a spacing of 5 to 50 microns and a height of 10 to 300 microns and a diameter of 10 to 200 microns. It is also advantageously possible to use notches, terraces, steps or sharp impact edges between and on the walls and on the base, in one embodiment.

When the fluid front flowing in through the trigger channel (12) in the capillary stop (10) reaches the height of the base of the feed channel (4), the liquid in the feedchannel (4) combines with that in the stop (10). The capillary stop (10) is then removed and the fluid flows away through the outlet channel (17).

The trigger channel (12) has greater capillarity than the reservoir (6). This ensures that the trigger channel (12) and the capillary stop (10) are filled.

The trigger channel (12) has a depth of 10 to 200 microns and a width of 20 to 300 microns. It is substantially rectangular in cross-section, particularly tub-shaped or semicircular, or is roughly triangular in shape. Because of the high capillarity of the trigger channel (12), there is still some fluid in the channel (12) after the filling of the capillary stop (10).

The channel volume of the fluid channel (12) should be less than 5%, in particular 1% of the reservoir volume, because of this lost amount of fluid. With a reservoir volume size of 10 microliters, the volume of the bypass (12) should thus be less than 0.5 microliters, particularly less than 0.1 microliters.

The capillary stop has a length of 200 to 2000 microns and a depth of 10 to 500 microns.

Because of the ramp in the capillary stop (10) and the step at the feed channel (4), the depth in the capillary stop (10) varies over a wide range.

The maximum depth, i.e. the depth of the base underneath the inlet of the feed channel (4), is between 200 and 500 microns. This ensures that a step of at least 100 microns to 500 microns is formed between the bottom of the feed channel (4) and the bottom of the capillary stop (10).

As the depth of the capillary stop (10) exceeds the depth of the outlet channel (17), a residual amount of fluid remains in the capillary stop (10). Depending on the capillarity of the fluid structures following the capillary stop, the capillary stop (10) may also remain completely full, i.e. when the capillary force of the following fluid-carrying structures is not enough to empty them. In order to reduce this lost quantity of fluid, the volume of the capillary stop (10) should be less than 10%, more particularly 2% of the reservoir volume.

With a volume of the reservoir (6) of 10 microliters the volume of the capillary stop should be less than 1 microliter, more particularly less than 0.2 microliters.

As the capillary stop is emptied to at most 50% after overcoming the stop, in the example described above 0.5 microliters, preferably in particular 0.1 microliters of fluid remain as the lost amount in the capillary stop (10).

As soon as the capillary stop (10) has been short-circuited or overcome by fluid from the trigger channel (12), the fluid or plasma in the reservoir (6) flows away via the supply channel (5), the capillary stop (10) and the outlet channel (17). The fluid then flows into or through substance or reagent chambers and/or reagent depots and dissolves the chemical substances deposited therein.

For a particular dissolution process, it is necessary to have a defined and substantially constant volume flow of fluid.

Figure 6:
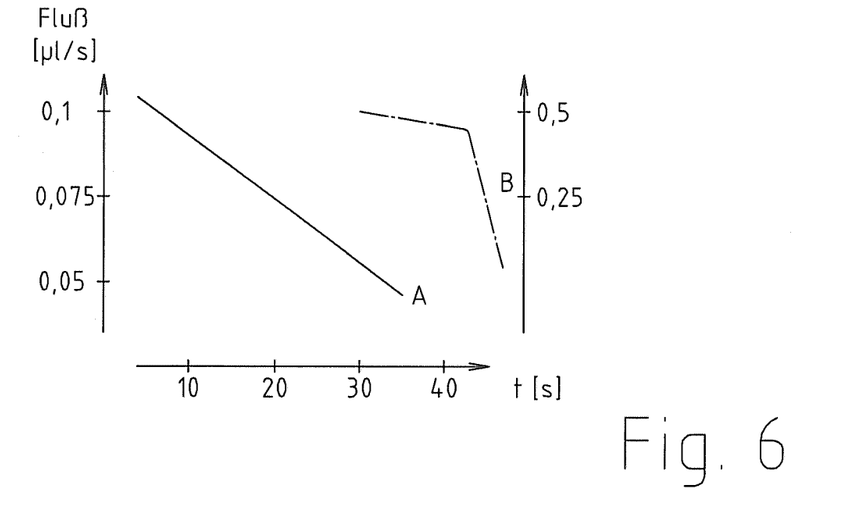
FIG. 6: Volume flows in the analysis area using a reservoir (curve B; without a reservoir: curve A)

FIG. 6 shows in curve B the volume flow in the outlet channel (17) after the bridging of the capillary stop (10) according to FIG. 4.

It is apparent that there is a substantially constant volume flow of the fluid or plasma for a specific length of time.

In the exemplary curve A according to FIG. 6, it is apparent that after the addition of 20 microliters of blood at time t=0, the volume flow out of the inlet chamber has decreased after 30 seconds from a volume flow which was more than 0.1 microliters per second at this time to about 0.05 microliters per second. Curve A is obtained by measuring the flow in the feed channel (5).

A reservoir (6) with a volume of 5 microliters is full after about 40 to 60 seconds. After another 5 to 30 seconds approximately, the capillary stop (10) is full and thus short-circuited.

A fluid current then starts in the outlet channel (17), as shown in curve B. This may be 2 to 50 times the volume flow according to curve A, as the volume flow is not braked by a filtering process. According to curve B, the volume flow after emptying the reservoir (6) is about 0.5 microliters per second and decreases slightly over time.

This outflow current in the channel (17) is fed from the reservoir (6) and from the feed channel (4).

After a length of time that is dependent on the quantity contained in the reservoir, in the present instance about 10 seconds, the reservoir (6) is totally empty again, so that the volume flow in the outlet channel (17) is reduced to the feed current supplied from the inlet chamber (2) and the feed channel (4).

Advantageously, the volume flow of fluid in an outlet channel (17) and/or a subsequent substance depot and/or a subsequent reaction chamber after a reservoir (6) has been filled for a period of 5 seconds to 100 seconds should assume a uniform value of 0.05 microliters per second up to 10 microliters per second.

When a drop of blood is used, i.e. when the volume to be filtered is from 5 microliters to 20 microliters, the volume flow of filtered plasma during the emptying of the reservoir should take place over a period of from 5 seconds to more than 30 seconds with a uniform volume flow of 0.1 microliters per second up to 2 microliterliters per second.

By a uniform value for the volume flow is meant that the flow value in the time interval specified varies by not more than 30%.

Reference Numerals

1—microfluidic apparatus
2—inlet chamber
3—membrane
4—first channel
5—second channel
6—reservoir
7—substrate carrier
8—trench
9—ventilation
10—fluid stop
11—direction of flow
12—trigger channel
13—channel entrance
14—structural element
15—vertical fluid elements
16—widened end of trench
17—outlet channel
18—transition region
20—fluid
21—lid
22—vertical throughflow opening
23—reagent
24—detectors
25—analysis chamber
26—inlet opening
41—recess
42—attachment
45—indentation

The invention claimed is:

1. A microfluid dispensing apparatus (1) for producing a blood plasma volume flow that is uniform over time, comprising:
  a device (3) for separating particles from the blood plasma volume,
  a first channel (4) for carrying the blood plasma volume away after the separation,
  a fluid stop (10) into which the first channel (4) opens, where the fluid stop (10) is arranged to stop the flow of the blood plasma volume intermittently,
  a second channel (5) disposed upstream and adjacent to the fluid stop (10), where the second channel (5) branches off from the first channel (4), and
  a reservoir (6) containing a reagent for interacting with the blood plasma volume, the reservoir being connected to the second channel, where: (i) the reservoir (6) is a chamber having an inlet cross-section of substantially a same cross-section of the second channel (5), and having a following cross-section that at least one of gradually and continuously widens out to at least five times that of the inlet cross-section, (ii) a depth of the reservoir (6) is 1.2 to 5 times a depth of the first channel (4), (iii) the reservoir (6) is laterally bounded by a trench (8), and (iv) an angle between a direction of flow of the blood plasma volume in the reservoir (6) and one edge of the trench is less than 70°, such that during the filling of the reservoir (6) a fluid interface of the flowing blood plasma runs along the edge of the trench.

2. The microfluid dispensing apparatus according to claim 1, wherein the reservoir chamber (6) has a volume of 0.1 to 50 microliters.

3. The microfluid dispensing apparatus according to claim 1, wherein in the inlet region of the reservoir (6) steps are arranged, so that terraces are formed by different step depths.

4. The microfluid dispensing apparatus according to claim 3, wherein in the inlet region of the reservoir (6) there is a ramp.

5. The microfluid dispensing apparatus according to claim 1, wherein the trench (8) forms a vent (9) for the reservoir (6).

6. The microfluid dispensing apparatus according to claim 1, further comprising a trigger channel (12), which branches off downstream from the reservoir (6) and forms a fluidic connection between the reservoir (6) and the fluid stop (10).

7. The microfluid dispensing apparatus according to claim 6, wherein the trigger channel (12) has a smaller cross-section than the reservoir (6), so that a capillary effect of the trigger channel (12) is greater by comparison than a capillary effect of the reservoir (6).

8. The microfluid dispensing apparatus according to claim 6, wherein a channel volume of the trigger channel (12) is one of: (i) at most 5% of a volume of the reservoir, and (ii) 0.02 to 0.2 microliters.

9. The microfluid dispensing apparatus according to claim 1, wherein the fluid stop (10) is formed by an area in the channel or chamber comprising hydrophobic material, and wherein the wetting of the material causes the fluid stop (10) to become hydrophilic by chemical and/or physical reaction, so that the fluid stop (16) is removed by the reaction after a time delay.

10. The apparatus according to claim 9, wherein a surface of the fluid stop (10) is rough, as a result of which fluid constituents can adhere physically to the surface, so that hydrophilic wetting can take place.

11. The microfluid dispensing apparatus according to claim 9, wherein hydrophilisation is able to take place by chemical binding of fluid constituents to the substrate or a ligand in the fluid stop (10).

12. The microfluid dispensing apparatus according to claim 1, wherein a depth of the fluid stop (10) in a mouth region of the first channel (4) is greater than a depth of the first channel, so that a capillary stop (10) is formed.

13. The microfluid dispensing apparatus according to claim 12, wherein the depth of the fluid stop (10) is at least twice the depth of the first channel (4).

14. The microfluid dispensing apparatus according to claim 13, wherein the depth of the fluid stop (10) is one of: (i) 0.1 to 1 millimeters, and (ii) 0.2 millimeters to 0.5 millimeters.

15. The microfluid dispensing apparatus according to claim 12, further comprising a trigger channel (12), which branches off downstream from the reservoir (6) and forms a fluidic connection between the reservoir (6) and the fluid stop (10), wherein the depth of the fluid stop (10) in a region adjoining the trigger channel (12) corresponds to a depth of the trigger channel (12) and wherein the depth of the fluid stop (10) increases continuously up to the mouth region of the first channel (4).

16. The microfluid dispensing apparatus according to claim 1, wherein the reservoir (6) has an asymmetrical shape at an end thereof.

* * * * *